United States Patent [19]

Balani et al.

[11] Patent Number: 5,188,950
[45] Date of Patent: Feb. 23, 1993

[54] METHOD OF PREPARING HIV PROTEASE INHIBITORS

[75] Inventors: Suresh K. Balani, Hatfield; Harri G. Ramjit; Steven M. Pitzenberger, both of Lansdale; Michael S. Schwartz, Glenside, all of Pa.; Anthony Y. H. Lu, Westfield, N.J.

[73] Assignee: Merck & Co., Inc., Rahway, N.J.

[21] Appl. No.: 845,520

[22] Filed: Feb. 27, 1992

Related U.S. Application Data

[63] Continuation of Ser. No. 771,026, Oct. 1, 1991, abandoned, which is a continuation of Ser. No. 595,909, Oct. 11, 1990, abandoned.

[51] Int. Cl.$^5$ ............................................. C12P 17/14
[52] U.S. Cl. .................................... 435/120; 544/165
[58] Field of Search ......................... 544/165; 435/120

[56] References Cited

U.S. PATENT DOCUMENTS

| | | | |
|---|---|---|---|
| 4,537,989 | 8/1985 | Ono et al. | 544/165 |
| 4,661,473 | 3/1984 | Boger | 514/16 |
| 4,758,563 | 7/1988 | Grous et al. | 544/165 |

OTHER PUBLICATIONS

Evans, B. E. et al., "A Sterocontrolled Synthesis . . . " Proc. Am. Pept. Symp., 9, 743 (1985) (Evans II).

Luly, J. R. et al., "A Synthesis of Protected Aminoalkyl Epoxides," J. Org. Chem. 52, 1487 (1987).
ASM News, vol. 56, No. 7 (Jul., 1990) at 368.
Crawford, S. et al., "A Deletion Mutant in . . . pol . . . Blocks Proteolytic Processing . . . ," J. Virol. 53, 899 (1985).
Power, M. D. et al., "Nucleotide Sequence of SRV-1 . . . ," Science 231, 1567 (1986).
Azri, S. et al., In Vitro Toxicology 3, 309 (1990).
Smith, P. F. et al., Life Sciences 36, 1367 (1985).
Krundieck, C. L. et al., Analytical Biochemistry 104, 118 (1980).
Chapman, D. E. et al., Drug Metabolism and Disposition, 18, 929 (1990).

Primary Examiner—Robert W. Ramsuer
Attorney, Agent, or Firm—Roy D. Meredith; Charles M. Caruso

[57] ABSTRACT

Novel dipeptide isosteres are the biotransformed products after incubation with rat liver slices. They inhibit HIV protease, and are useful in the prevention or treatment of infection by HIV and the treatment of AIDS, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS and methods of preventing or treating infection by HIV are also described.

2 Claims, No Drawings

METHOD OF PREPARING HIV PROTEASE INHIBITORS

This is a continuation of application Ser. No. 771,026 filed Oct. 1, 1991, abandoned, which is a continuation of Ser. No. 07/595,909, filed Oct. 11, 1990, abandoned.

This application is related to Merck Case 18025.

The present invention is concerned with compounds which inhibit the protease encoded by human immunodeficiency virus (HIV). The compounds, or pharmaceutically acceptable salts thereof, are of value in the prevention of infection by HIV, the treatment of infection by HIV and the treatment of the resulting acquired immune deficiency syndrome (AIDS). The present invention also relates to pharmaceutical compositions containing the compounds and to a method of use of the present compounds with or without other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Interruption of this processing appears to prevent the production of normally infectious virus. For example, Crawford, S. et al., J. Virol., 53, 899, 1985, demonstrated that genetic deletion mutations of the protease in murine leukemia virus which prevent processing of precursor structural proteins result in non-infectious viral particles. Unprocessed structural proteins also have been observed in clones of non-infectious HIV strains isolated from human patients. These results suggest that inhibition of the HIV protease represents a viable method for the treatment of AIDS and the prevention or treatment of infection by HIV.

Nucleotide sequencing of HIV shows the presence of a pol gene in one open reading frame [Ratner, L. et al, Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

Applicants demonstrate that the compounds of this invention are inhibitors of HIV protease.

BRIEF DESCRIPTION OF THE INVENTION

Biotransformed compounds, as herein defined, are disclosed. These compounds are useful in the inhibition of HIV protease, the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION

This invention is concerned with the use of two compounds shown below, combinations thereof, or pharmaceutically acceptable salts thereof, in the inhibition of HIV protease, the prevention or treatment of infection by HIV and in the treatment of the resulting acquired immune deficiency syndrome (AIDS). Biotransformed compounds of L-689,502 (an HIV protease inhibitor) are defined as follows:

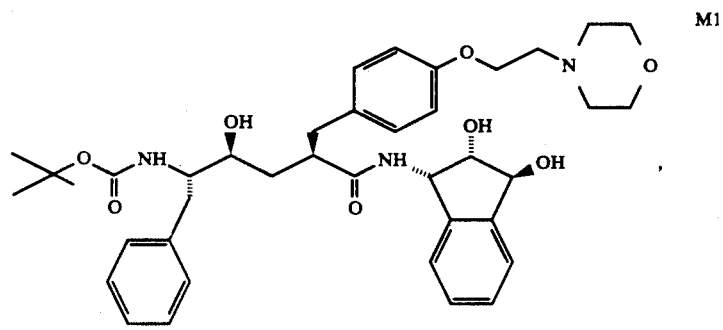

or

-continued

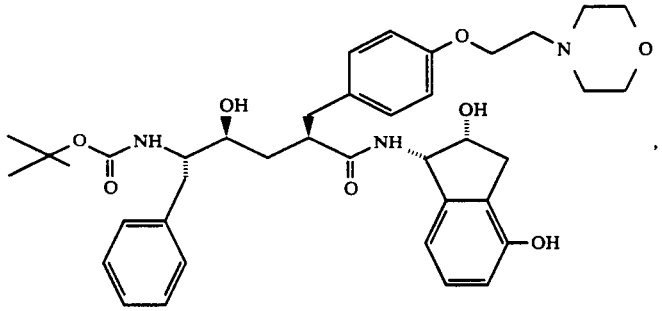
M2 or pharmaceutically acceptable salt, hydrate or ester thereof.

The pharmaceutically-acceptable salts of the compounds of the present invention (in the form of water- or oil- soluble or dispersible products) include whenever appropriate the conventional non-toxic salts or the quaternary ammonium salts of these compounds, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfa&e, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, and undecanoate. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Hydrates or esters are also encompassed by the present invention. Such hydrates or esters are those which would readily occur to the skilled artisan. and include, for example, $C_{1-4}$ alkyl esters.

The compounds of the present inventions are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

Dosage levels of the order of 0.02 to 5.0 or 10.0 g per day are useful in the treatment or prevention of the above-indicated conditions, with oral doses up to two to five times higher. For example, infection by HIV is effectively treated by the administration of from 10 to 50 mg of compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age of the patient, body weight, general health, sex, diet, mode and time of administration, rate of excretion, drug combination, the severity of the particular condition, and the host undergoing therapy.

The present invention is also directed to combinations of the HIV reverse transcriptase inhibitor compounds with one or more agents useful in the treatment of AIDS. For example, the compounds of this invention may be effectively administered, whether at periods of pre-exposure and/or post-exposure, in combination with effective amounts of other AIDS antivirals, immunomodulators, anti-infectives, or vaccines.

SYNTHESIS OF L-689,502

The preparation and synthesis follows, in general, U.S. Pat. No. 4,661,473; Evans, B. E. et al, *J. Org. Chem.*, 50, 4615, (1985) and Evans, B. E. et al., "A Stereocontrolled Synthesis of Hydroxyethylene Dipeptide Isosteres," Proc. Am. Pept. Symp., 9, 743–6(1985), and Luly, J. R. et al, J. Org. Chem, 52, 1487 (1987), all herein incorporated by reference. All temperatures are in degrees centigrade, unless indicated otherwise.

EXAMPLE 1

Preparation of N-(cis-2(R)-hydroxy-1(S)-indanyl)-5(S)-(1,1-dimethylethoxycarbonylamino)-4(S)-hydroxy-6-phenyl-2(R)-[(4-(2-(4-morpholinyl)ethoxy)phenyl) methyl]-hexanamide. L-689,502

Step A: Preparation of N-3(S)-[(1,1-Dimethylethoxycarbonyl)amino]-2(RS)-hydroxy-4-phenyl-1-trimethylsilyl butane To a stirred suspension of magnesium turnings (9.79 g, 403 mmol) in dry diethyl ether (200 mL) under nitrogen was added chloromethyltrimethylsilane (50 mL, 358 mmol). The reaction was initiated by gentle warming and then was cooled in an ice bath to maintain gentle reflux. After exotherm was complete the reaction was stirred at room temperature for 1 hour then cooled to −78° C. in a dry ice/acetone bath. To the solution of the Grignard was added dropwise with stirring a solution of N-2(S)-[(1,1-dimethylethoxycarbonyl)amino]-3-phenyl propionaldehyde (19.3 g, 77.4 mmol) in dry diethyl ether (250 mL) dropwise such that the temperature of the reaction remained below −55° C. The resultant gray suspension was allowed to warm to room temperature where it was stirred for 30 minutes then was quenched by pouring into a mixture of ice (500 g) and 10% citric acid (500 mL). The organic phase was collected and the aqueous phase was extracted with diethyl ether (3×300 mL). The combined organics were washed with 10% citric acid (1×300 mL) and brine (1×200 mL), dried over anhydrous magnesium sulfate, filtered, and concentrated to give crude N-3(S)-[(1,1-dimethylethoxycarbonyl)amino]-2(RS)-hydroxy-4-phenyl-1-trimethylsilyl butane (26.6 g, quantitative crude yield) as a yellow oil. An analytical sample was obtained by low pressure chromatography (silica gel, 230–400 mesh; diethyl ether:hexanes, 30%:70%) followed by recrystallization from heptane. mp=91°–95° C., elemental analysis. Calcd. for $C_{18}H_{31}NO_3Si$ (337.53):

C=64.05, H=9.26, N=4.15; Found: C=64.05, H=9.13, N=4.22; $[a]_D^{20}$=−40.0°.

Step B: Preparation of 3(S)-Amino-4-phenyl-1-butene

To a stirred solution of the product of Step A (22.8 g, 67.5 mmoL) in dry methylene chloride (400 mL) cooled in an ice bath and under nitrogen was added in a fine stream boron trifluoride etherate (43 mL, 345 mmol). The solution was allowed to warm to room temperature where it was stirred for 4 days. Reaction was cooled in an ice bath and quenched by the dropwise addition of 10% sodium hydroxide (400 mL). The organic phase was collected and the aqueous phase was extracted with methylene chloride (2×250 mL). The combined organics were washed with brine (1×200 mL), dried over anhydrous magnesium sulfate, filtered, and concentrated to give crude 3(S)-amino-4-phenyl-1-butene (14.2 g) as a yellow oil.

Step C: Preparation of N-3(S)-[(1,1-Dimethyethoxycarbonyl)amino]-4-phenyl-1-butene A solution of the product of Step B (14.2 g) and di-tert-butyl dicarbonate (31.0 g, 142 mmoL) in dry methylene chloride (200 mL) was stirred at room temperature for 18 hours, washed with 10% citric acid (3×100 mL), water (1×100 mL), sat'd. sodium bicarbonate (3×125 mL), and brine (1×250 mL), dried over anhydrous magnesium sulfate, filtered and concentrated to yield crude N-3(S)-l[(1,1-dimethylethoxycarbonyl)amino]-4-phenylbutene (34.6 g) as a yellow oil. Crude product was purified by low pressure chromatography (silica gel, 230–400 mesh, 10×20 cm column; diethylether:-hexanes, 20%:80%) to yield N-3(S)-[(1,1-dimethylethoxylcarbonyl)amino]-4-phenyl-1-butene (16.3 g, 97.6% yield) as a white solid. An analytical sample was obtained by recrystallization from heptane. mp=67.5°–68.5° C.; elemental analysis, Calcd. for $C_{15}H_{21}NO_2$ (247.34):

C=72.84, H=8.56, N=5.66. Found: C=72.78, H=8.76, N=5.64.

Step D: Preparation of 1(R)-[1'(S)-(1,1-Dimethylethoxycarbonyl)amino-2-phenylethyl]oxirane To a solution of the product of Step C (9.4 g, 38 mmol) in dry methylene chloride (100 mL) cooled in an ice bath and under nitrogen was added 3-chloroperoxybenzoic acid (technical grade, 80–85%; 41 g, 200 mmol). The mixture was stirred at 0° C. for 18 hours and 25° C. for 23 hours, then diluted with diethyl ether (300 mL), and poured in ice cold aqueous 10% sodium sulfite (1 L). The organic layer was collected and the aqueous layer was extracted with diethyl ether (3×100 mL). The combined organics were washed with 10% sodium sulfite (3×100 mL), satd. sodium bicarbonate (3×100 mL), and brine (1×100 mL), dried over anhydrous sodium sulfate, filtered and concentrated to give a white solid. Crude product was purified by low pressure chromatography (silica gel 230–400 mesh, 8×15 cm column; ethyl acetate:hexanes, 25%:75%) to yield 1(R)-[1'(S)-(1,1-dimethylethoxycarbonyl)amino-2-phenylethyl]oxirane (7.0 g, 70% yield) as a clear oil which crystallized upon standing. An analytical sample was obtained by recrystallization from heptane.

mp=51.5°-52° C., elemental analysis, Calcd. for C$_{15}$H$_{21}$NO$_2$ (263.34):

C=68.42, H=8.04, N=5.32. Found: C=68.22, H=8.26, N=5.29; [a]$_D^{20}$=1.34°.

Step E: Preparation of (5S,1'S)-3-carboethoxy-5-(1-((1',1'-dimethylethoxycarbonyl)amino)-2-phenylethyl)-dihydrofuran-2-(3H)-one The product from Step D, 9.93 g, was dissolved in 100 mL of absolute ethanol and added to a solution of 2.6 g of sodium and 20.1 mL of diethyl malonate in 170 mL of absolute ethanol. After stirring overnite, the reaction was acidified to pH 4 with 10% citric acid and extracted with 2×500 mL of ether. The combined organic extracts were washed 1×500 mL H$_2$O, 1×500 mL sat'd NaHCO$_3$, 1×500 mL sat'd brine and dried over MgSO$_4$. The solvents were removed and the crude product purified by low pressure chromatography on silica gel eluting with 50% ether/hexanes (or EtOAc/hexanes). The yield of semi-solid product was 10.6 g. The later fractions contained 2.5 g of the undesired 5 R isomer as a white solid.

Step F: Preparation of (5S,1'S)-3-carboethoxy-3-(4-benzyloxyphenylmethyl)-5-[1-(1,1-dimethylethoxycarbonyl)amino)-2-phenylethyl]dihydrofuran-2-(3H)-one To a stirred solution of (5S,1'S)-3-carboethoxy-5-[1-((1',1'-dimethylethoxycarbonyl)amino)-7-phenylethyl)-dihydrofuran-2-(3H)-one (product of Step E), 2 g (5.3 mmol) in 25 mL of absolute ethanol was added a solution of 0.13 g of sodium in 2.2 mL of absolute ethanol followed by 1.30 g (5.5 mmol) of 4-benzyloxybenzyl chloride. The solution was heated to 50° C. under nitrogen for 1 hour, then cooled in an ice bath and acidified with 20 mL of 10% citric acid and diluted with 200 mL of water. The mixture was extracted with 3×100 mL of ether and the combined ether extracts washed with 50 mL of water, 200 mL of sat'd NaHCO$_3$ and dried over MgSO$_4$. Removal of solvents under reduced pressure and purification by low pressure chromatography on silica gel, eluting with 40% ether in hexanes gave 1.56 g (51% yield) of a clear colorless glass essentially homogeneous by TLC (50% ether/hexanes).

Step G: Preparation of (3R,5S,1'S)-3-(4-benzyloxyphenylmethyl)-5-(1((1,1-dimethylethoxycarbonyl)amino)-2-phenylethyl)-dihydrofuran-2-(3H)-one The product of Step F, 13.6 g, was dissolved in 250 mL of 1,2-dimethoxyethane, and to it was added 117 mL of 1M lithium hydroxide at room temperature. After stirring for 12 hours, the solvents were removed under reduced pressure, the residue suspended in 200 mL of 10% citric acid and extracted 3×500 mL of diethyl ether. The combined ether extracts were washed with 500 mL of brine, dried (MgSO$_4$) and the concentrated to dryness. The residue was dissolved in 250 mL of toluene, heated to reflux for 12 hours, then concentrated to dryness under reduced pressure. Purification by medium pressure chromatography over silica gel eluting with 15% ethyl acetate/hexanes gave 3.2 g of the 3R-lactone as a clear foam. Further elution with the same solvents gave 6.15 g of the 3S-lactone as a white solid.

Step H: Preparation of N'-(1,1-dimethylethoxycarbonyl)-5(S)-amino-4(S)-(1',1'-dimethylethyl-1,1-dimethylsilyloxy)-6-phenyl-2(R)-(4-benzyloxyphenylmethyl-hexanoic acid The product of Step G, 0.6 g, was dissolved in 30 mL of a 2:1 mixture of ethylene glycol dimethyl ether/water, and to it was added 5 mL of 1M lithium hydroxide at room temperature. After stirring for 1 hour, the mixture was partitioned between 200 mL chloroform and 20 mL 10% citric acid. The layers were separated and the aqueous phase extracted with 3×20 mL chloroform. The combined organic layers were dried (Na$_2$SO$_4$) and the solvent removed to yield 0.56 g of the crude hydroxy acid. This residue was dissolved in 5 mL of dry DMF and 0.845 g tert-butyl dimethylsilyl chloride and 0.725 g of imidazole were added. After stirring for 18 hours, the reaction was poured into 50 mL of water and extracted with 3×20 mL of ethyl acetate. The combined organic extracts were washed with 3×20 mL of 10% citric acid, 1×20 mL of water, 3×10 mL of saturated aqueous solution of Na$_2$CO$_3$, and 20 mL of brine. After drying (Na$_2$SO$_4$), the solvent was removed and the resulting residue dissolved in a mixture of 5 mL of THF, 5 mL of glacial acetic acid, and 2 mL of water. The mixture was stirred for 4 hours, then poured into 50 mL of water and extracted with 3×20 mL of ether. The combined ether extracts were washed with 2×20 mL of water, brine, dried (Na$_2$SO$_4$), and the solvent removed. Purification by medium pressure chromatography over silica gel, eluting with MeOH/CHCl$_3$ gave 0.60 g of the product as a white glassy solid.

Step I: Resolution of 1-Amino-2-hydroxyindan

From the known racemic 1-amino-2-hydroxyindan, the resolution was carried out as described for the 3-amino-1,2-dihydroxyindan in Example 7 below (Steps D and E). The (1S,2R)-1-amino-2-hydroxyindan resulting from saponification of the higher R$_f$ diastereomer was shown to have an a$_D$ of −58° (c=1.0, CHCl$_3$). The (1R, 2S)-1-amino-2-hydroxyindan resulting from saponification of the lower R$_f$ diastereomer was found to have an a$_D$ of +62° (c=1.0, CHCl$_3$).

Step J: Preparation of N-(2(R)-hydroxy-1(S)-indanyl)-5(S)-(1,1-dimethylethoxycarbonylamino)-4(S)-hydroxy-6-phenyl-2(R)-(4-benzyloxyphenylmethyl) hexanamide The product from Step H, 0.12 g, was dissolved in 2 ml dry DMF and to it was added 40 mg of 1(S)-amino-2(R)-hydroxyindane, (Step I) 25 mg of 1-hydroxybenzotriazole hydrate and 70 mg of dimethyl-3-(3-dimethyl aminopropyl)carbodiimide hydrochloride. Triethylamine was added to the stirred solution until the pH was 8.5 (32 mL). After stirring for concentrated to dryness under reduced pressure, the residue was dissolved in 100 mL of chloroform and worked with 1×50 mL of 10% citric acid, 1×50 mL H$_2$O, 1×50 mL sat'd NaHCO$_3$, dried over MgSO$_4$ and concentrated to dryness. The residue was dissolved in 1 mL of tetrahydrofuran and added to 2 mL of 1M tetrabutylammonium fluoride in THF. After stirring overnight at room temperature the reaction mixture was diluted with 10 mL of 10% citric acid and the white precipitate collected by filtration. The product was purified by low pressure chromatography on silica gel eluting with 2% methanol/CH$_2$Cl$_2$ to give 85 mg of product which was essentially homogeneous by TLC (3% methanol/CH$_2$Cl$_2$).

Step K: Preparation of N-(2(R)-hydroxy-1(S)-indanyl)-5(S)-(1,1-dimethylethoxycarbonylamino)-4(S)-hydroxy-6-phenyl-2(R)-(4-hydroxyphenylmethyl)hexanamide The product of Step J, 85 mg was dissolved in 10 mL of methanol and 10 mL of THF, and to it was added 0.10 g of 10% palladium on carbon. The mixture was stirred under an atmosphere of hydrogen for 48 hours at room temperature, then filtered and concentrated to dryness. The residue was dissolved in 10 mL of hot ethanol and 20 mL water was added. On cooling the white solid precipitate was collected and dried under vacuum over P$_2$O$_5$. The yield was 72 mg (98% yield) of pure product: mp 218°–219° C. (effervesces, sinters at 215) elemental analysis, Calc'd for C$_{33}$H$_{40}$N$_2$O$_6$: (560.696):

C, 70.69; H, 7.19; N, 5.00; Found: C, 70.62; H, 7.39; N, 4.79.

Step L: Preparation of N-(cis-2(R)-hydroxy-1(S)-indanyl)-5(S)-[1,1-dimethylethoxycarbonylamino)-4(S)-hydroxy-6-phenyl-2(R)-[(4-(2-(4-morpholinyl)ethoxy)phenyl]methyl]hexanamide A stirred mixture of Step K product, N-(2(R)-hydroxy-1(S)-indanyl)-5(S)-[1,1-dimethylethoxycarbonyl)amino]-4(S)-hydroxy-6-phenyl-2(R)-(4-hydroxyphenylmethyl) hexanamide (0.50 g, 0.9 mmol), anhydrous cesium carbonate (1.0 g, 3 mmol) and N-(2-chloroethyl) morpholine, free base (2.35 g, 17 mmole) in 100 mL of anhydrous dioxane was heated to 80° C. (internal temperature) for 3 hrs. After cooling to room temperature the mixture was diluted with chloroform (50 mL) filtered, concentrated to dryness under reduced pressure, and the residue triturated with 50 ml of anhydrous ether and 10 mL of ethyl acetate. The while solid product was collected and dried under vacuum over P$_2$O$_5$. The yield was 0.54 g (89%) of pure product: mp 195°–197° C. Elemental analysis, Calc'd. for C$_3$H$_{51}$N$_3$O: (673.856):

C, 69.52 H, 7.63; N, 6.23; Found: C, 69.19 H, 7.45., N, 6.15.

maleate hydrate:

mp 112°–113° C. dec. elemental analysis, Calc'd. for C$_{39}$H$_{51}$N$_3$O$_7$.C$_4$H$_4$O$_4$.H$_2$O: (807.946);

C, 63.92 H, 7.11; N, 5.20; Found: C, 64.23 H, 6.94; N, 5.10.

EXAMPLE 2

Biotransformation of L-689,502 by Rat Liver Slices

L-689,502 (5.65 μmole) was incubated at pH 7.4, 37° C., with rat liver slices (1 cm wide, 200–300μ 3.7 g) in 100 ml of Williams' Medium E (composition described in Sigma commercial circular, pages 1–5, herein incorporated by reference for this purpose). A gradual increase in the metabolites in an organic extract of the medium was observed over a period of 5 hours when ~31% of .he drug was metabolized. Three of the major metabolites M1 (6.1% of the total metabolites) and M2 (6.3%) and M4 (12.1%) were characterized by $^1$H-NMR and FAB/Mass spectroscopies. Exact mass measurements, by high resolution FAB/MS, for M1 and M2 gave a molecular ion at m/z 690.375305, which computed to an empirical formula of C$_{39}$H$_{52}$N$_3$O$_8$ for the protonated form. The M4 peak was also matched with a synthetic standard by HPLC, MS and NMR. The structures were found to be as follows:

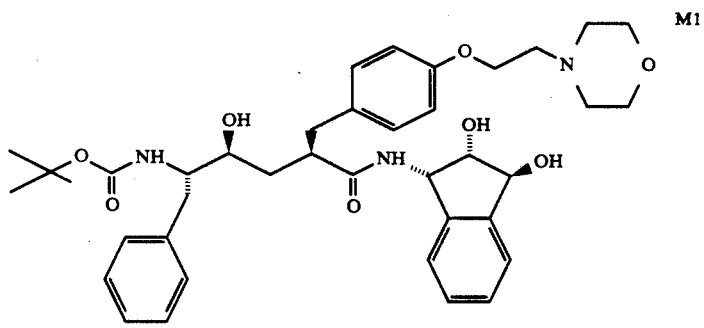

L-695,938
N-[2(S),3(S)-dihydroxy-1(S)-indanyl]-5(S)-(1,1-dimethylethoxycarbonylamino)-4(s)-hydroxy-6-phenyl-2(R)-{[4-(2-(4-morpholinyl)ethoxy)phenyl]methyl}-hexanamide

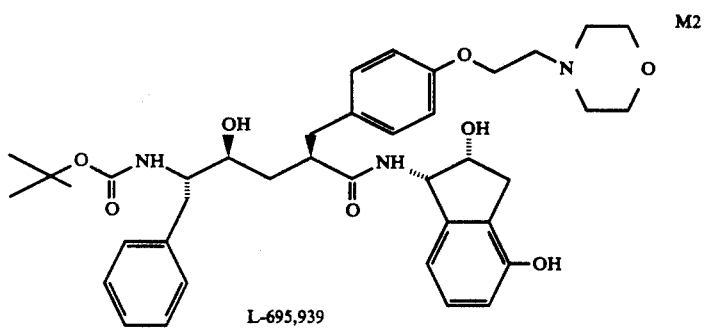

L-695,939
N-[2(R),4-dihydroxy-1(S)-indanyl]-5(S)-(1,1-dimethyl-ethoxycarbonylamino)-4(S)-hydroxy-6-phenyl-2(R)-{[4-(2-(4-morphlinyl)ethoxy)phenyl]methyl}hexanamide

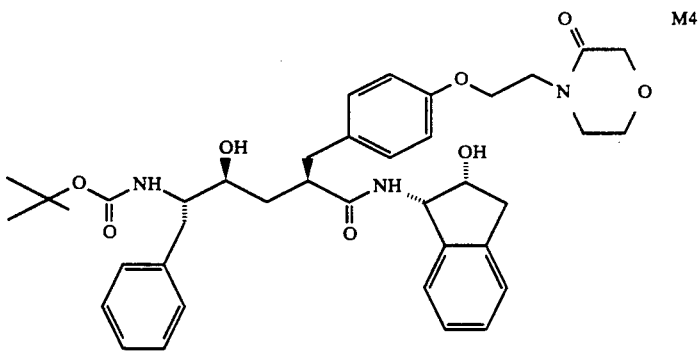

Additional analysis confirmed these structures.

EXAMPLE 3

Biotransformation of L-689,502 by Dog Liver Slices

Incubation of L-689,502 with dog liver slices indicated a similar metabolic profile on HPLC, as compared with biotransformation by rat liver slices. A different proportion of peaks was found, i.e., M1 (13.1% of the total metabolites), M2 (1.6%), and a small amount of M4.

EXAMPLE 4

Assay for Inhibition of Microbial Expressed Viral Protease

Inhibition studies of the reaction of the protease expressed in *Escherichia coli* with a peptide substrate [Val-Ser-Gln-Asn-(betanapthyl)Ala-Pro-Ile-Val, 0.665 mg/mL at the time the reaction is initiated] were carried out. Aliquots of 40 μl of substrate in substrate buffer (60 mM Na acetate, pH 5.5, in 0.117% BSA) were combined with 10 μl aliquots of various concentrations of inhibitor. The reaction was initiated by the addition of 10 μl of 1.7 nM protease in a solution of 0.05M Na acetate, pH 5.5, in 10% glycerol, 1 mM DTT, 1 mM EDTA, and 64 μM octoxynol-9.5 to yield a final concentration of 283 pM protease. Incubation proceeded for 2 hours at 36° C. The reaction was quenched with 75 ul of 5% phosphoric acid. Products of the reaction were separated by HPLC. The extent of inhibition of the reaction was determined from the peak heights of the products. HPLC of the products, independently synthesized, proved quantitation standards and confirmation of the product composition.

The compounds M1,M2 and M4 of the present invention, as isolated from rat liver slices incubated with L-689,502, were found to have the following estimated activities:

| Compound | IC$_{50}$ |
| --- | --- |
| M1 | 2.7 nM |
| M2 | 1.3 nM |
| M4 | ~0.5 nM |
| L-689,502 | .93 nM |
| L-689,502 (recovered) | .95 nM |

EXAMPLE 5

Organic Synthesis of M1

Steps J through L of Example 1 are repeated except that 1(S)-amino-2(S)-hydroxy-3(S)-[4-benzyloxy]indane replaces 1(S)-amino-2(R)-hydroxyindane. The additional protecting group is removed in Step K.

EXAMPLE 6

Organic Synthesis of M2

Steps J through L of Example 1 are repeated except that 1(S)-amino-2(R)-hydroxy-4-[4-benzyloxy]indane replaces 1(S)-amino-2(R)-hydroxyindane. The additional protecting group is removed in Step K.

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A method of preparing the product compound of the structure

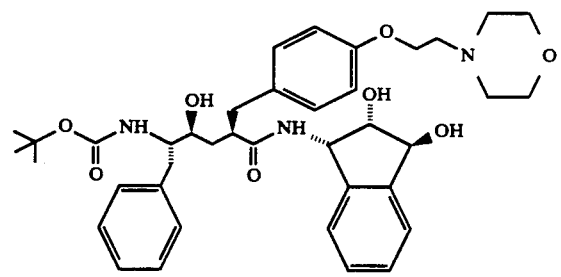

comprising the steps of
   (1) providing a quantity of substrate N-(cis-2(R)-hydroxy-1(S)-indanyl)-5(S)-(1,1-dimethylethoxycarbonylamino)-4(S)-hydroxy-6-phenyl-2(R)-((4-(2-(4-morpholinyl)ethoxy)phenyl)-methyl)-hexanamide,
   (2) incubating the substrate compound of step 1 with rat liver slices, and
   (3) isolating the product compound.

2. A method of preparing the product compound of the structure

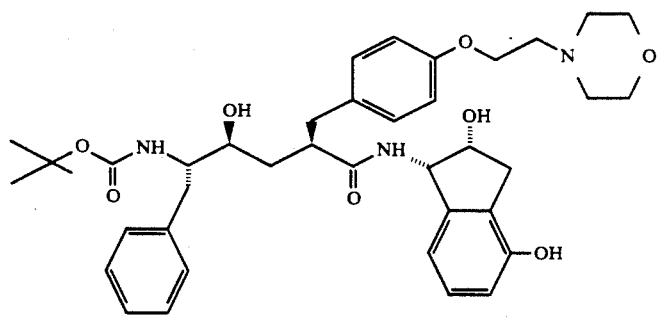
comprising the steps of
(1) providing a quantity of substrate N-(cis-2(R)-hydroxy-1(S)-indanyl)-5(S)-(1,1-dimethylethoxycarbonylamino)-4(S)-hydroxy-6-phenyl-2(R)-((4-(2-(4-morpholinyl)ethoxy)phenyl)-methyl)-hexanamide,
(2) incubating the substrate compound of step 1 with rat liver slices, and
(3) isolating the product compound.
* * * * *